United States Patent
Miyaoka (10) Patent No.: US 9,570,266 B2
(45) Date of Patent: Feb. 14, 2017

(54) X-RAY GENERATING APPARATUS

(71) Applicant: Shimadzu Corporation, Kyoto (JP)

(72) Inventor: Akihiro Miyaoka, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 15/135,668

(22) Filed: Apr. 22, 2016

(65) Prior Publication Data

US 2016/0329185 A1 Nov. 10, 2016

(30) Foreign Application Priority Data

May 8, 2015 (JP) .................. 2015-095467

(51) Int. Cl.
| | |
|---|---|
| *H01J 5/48* | (2006.01) |
| *H01J 19/64* | (2006.01) |
| *H01J 35/16* | (2006.01) |
| *H01J 37/16* | (2006.01) |
| *H05G 1/02* | (2006.01) |
| *H05G 1/04* | (2006.01) |
| *H01J 5/04* | (2006.01) |
| *H01J 5/02* | (2006.01) |
| *H01J 19/54* | (2006.01) |
| *A61B 6/00* | (2006.01) |

(52) U.S. Cl.
CPC .................. *H01J 35/16* (2013.01); *H01J 5/48* (2013.01); *H01J 37/16* (2013.01); *H05G 1/04* (2013.01);

(Continued)

(58) Field of Classification Search
CPC .............. H05G 1/00; H05G 1/02; H05G 1/04; H05G 1/26; H05G 1/52; H01J 1/00; H01J 1/02; H01J 1/18; H01J 1/36; H01J 1/40; H01J 1/46; H01J 1/88; H01J 5/00; H01J 5/02; H01J 5/04; H01J 5/12; H01J 5/18; H01J 5/20; H01J 5/22; H01J 5/48; H01J 19/00; H01J 19/54; H01J 19/56; H01J 19/64; H01J 35/00; H01J 35/02; H01J 35/025; H01J 35/04; H01J 35/08; H01J 35/14; H01J 35/16; H01J 35/165; H01J 35/18; H01J 37/00; H01J 37/16; H01J 37/165; H01J 2235/00; H01J 2235/08; H01J 2235/081; H01J 2235/083; H01J 2235/086; H01J 2235/087; H01J 2235/16; H01J 2235/161; H01J 2235/163; H01J 2235/186; A61B 6/00; A61B 6/40; A61B 6/44; A61B 2560/00; A61B 2560/04; A61B 2560/0406

See application file for complete search history.

(56) References Cited

U.S. PATENT DOCUMENTS 2,209,963 A * 8/1940 Du Mond ............... H01J 35/26 313/148
2,290,226 A * 7/1942 Du Mond ............... H01J 35/14 313/148

(Continued)

FOREIGN PATENT DOCUMENTS

| JP | 2000-090862 A | 3/2000 |
|---|---|---|
| JP | 2012-054045 A | 3/2012 |

*Primary Examiner* — Anastasia Midkiff
(74) *Attorney, Agent, or Firm* — Renner, Otto, Boisselle & Sklar, LLP (57) ABSTRACT

An x-ray generating apparatus comprises: a vacuum container having a main body, and a moving member coupled movably and airtightly to the main body via a vacuum bellows; and a guide mechanism, provided on an outer side of the vacuum container, for regulating the movement and inclination of the moving member in an approaching/separation direction with respect to an electron gun. The guide mechanism includes a guide portion where a guide flat surface along a plane orthogonal to a central axis of the electron beam is formed, the guide portion being provided on the main body side, a guided portion where a guided flat surface facing the guide flat surface is formed, the guided portion being provided on the moving member side, and at least three rolling elements placed between the guide flat surface and the guided flat surface.

7 Claims, 10 Drawing Sheets (52) U.S. Cl.
CPC .. *A61B 6/40* (2013.01); *A61B 6/44* (2013.01); *A61B 2560/0406* (2013.01); *H01J 5/02* (2013.01); *H01J 5/04* (2013.01); *H01J 19/54* (2013.01); *H01J 19/64* (2013.01); *H01J 2235/16* (2013.01); *H01J 2235/163* (2013.01); *H05G 1/02* (2013.01)

(56) References Cited

U.S. PATENT DOCUMENTS

| | | | | |
|---|---|---|---|---|
| 3,689,790 | A * | 9/1972 | Haas | H01J 35/24 |
| | | | | 313/30 |
| 3,737,698 | A * | 6/1973 | Carter | H01J 35/02 |
| | | | | 378/124 |
| 3,753,020 | A * | 8/1973 | Zingaro | H01J 35/12 |
| | | | | 313/149 |
| 3,794,872 | A * | 2/1974 | Haas | H01J 35/24 |
| | | | | 313/32 |
| 3,835,341 | A * | 9/1974 | Zingaro | H01J 35/18 |
| | | | | 378/140 |
| 2005/0190887 | A1* | 9/2005 | Kim | H01J 35/24 |
| | | | | 378/125 |
| 2014/0247921 | A1* | 9/2014 | Parker | H01J 35/10 |
| | | | | 378/125 |
| 2014/0314209 | A1* | 10/2014 | Parker | H01J 35/10 |
| | | | | 378/140 |

* cited by examiner

X-RAY GENERATING APPARATUS

BACKGROUND OF THE INVENTION

1. Technical Field

The present invention relates to an x-ray generating apparatus.

2. Description of the Related Art

X-ray generating apparatuses of a type that causes electrons to collide with a target in a vacuum container and generates x-rays include one using a reflection target that removes the x-rays in a different direction from the travel direction of the electrons, and one using a transmission target that removes the x-rays in substantially the same direction as the travel direction of the electrons.

Of them, the reflection target generally uses a bulk material. The reflection target is placed, some distance away from an x-ray irradiation window for removing x-rays from the vacuum container to the outside, in the rear of the container. In contrast, the transmission target generally adopts a structure of being laminated and formed integrally with the x-ray irradiation window. Accordingly, an x-ray focal spot is at the nearest position to the x-ray irradiation window. Accordingly, there is an advantage that the transmission target can increase a fluoroscopic magnification by being used in an apparatus that constructs a fluoroscopic image and a tomogram. However, conversely, the transmission target is laminated and formed into a thin film on one side of the x-ray irradiation window. Accordingly, there is a problem that the life of the transmission target is reduced by thermal damage due to electron irradiation.

For the purpose of increasing the life of such a transmission target, for example, JP-A-2000-90862 proposed to move a target freely to change a position to be irradiated with electrons on a target surface. JP-A-2000-90862 discloses a technology for, in an x-ray generating apparatus that uses an open vacuum container and includes a transmission target, moving the target via an O-ring and a vacuum bellows.

Figure 8:
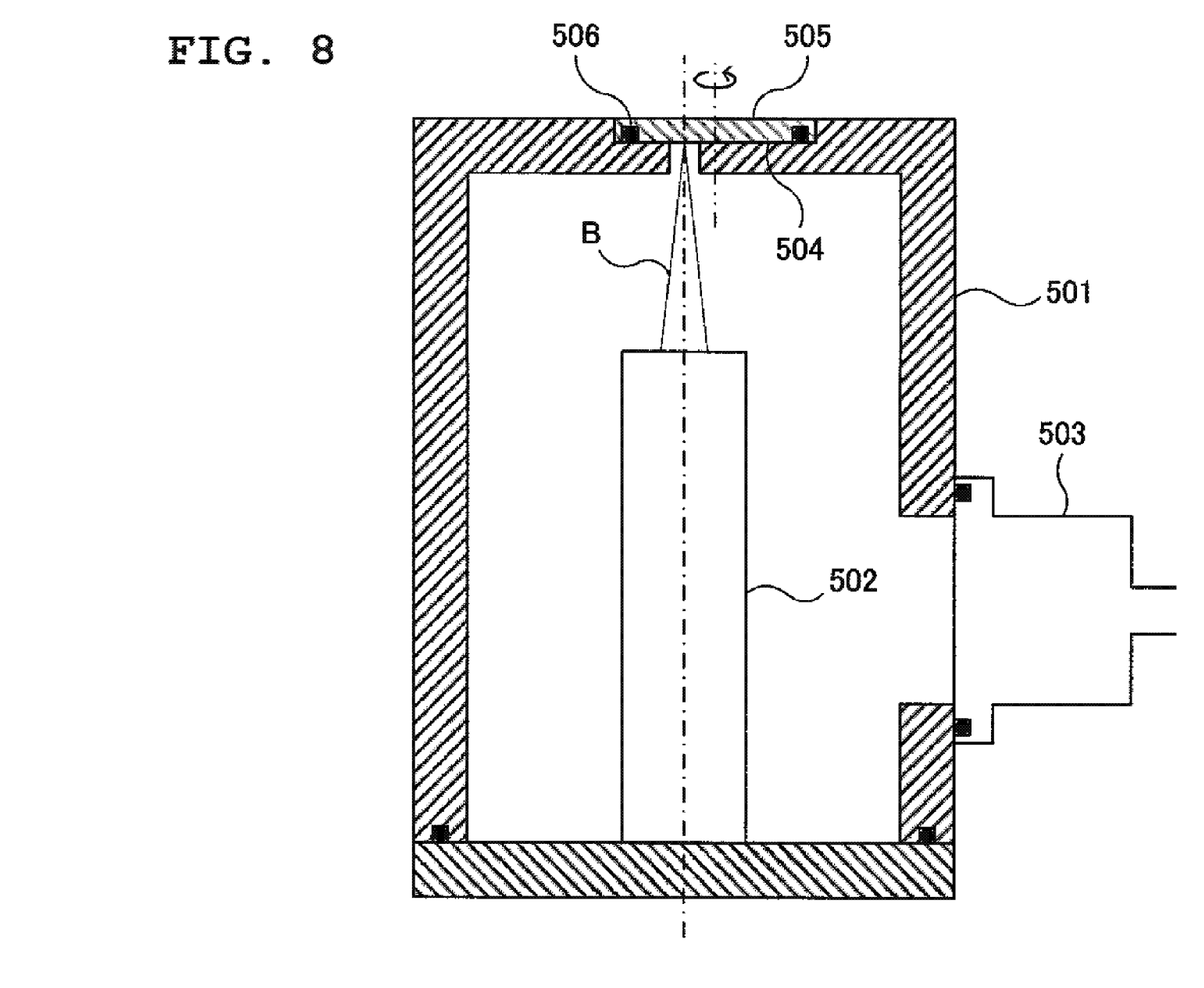
FIG. 8 is a schematic cross-sectional view illustrating a configuration example of an x-ray generating apparatus using an open vacuum container.

In the above proposal, FIG. 8 is a schematic cross-sectional view illustrating a configuration in a case of using a rubber O-ring. In an open-transmissive x-ray generating apparatus configured to accommodate, in a vacuum container 501, an electron gun 502 including an electron source and a group of electrodes for accelerating and focusing electrons from the electron source to freely evacuate the vacuum container 501 by a vacuum pump 503, an x-ray irradiation window 505 where a target 504 is integrally laminated and formed is mounted on the vacuum container 501 via an O-ring 506, and is rotationally moved at a position that is eccentric with respect to, for example, the track of an electron beam B from the electron gun 502. Accordingly, the position of irradiation of the electron beam B on the surface of the target 504 is changed.

Figure 9:
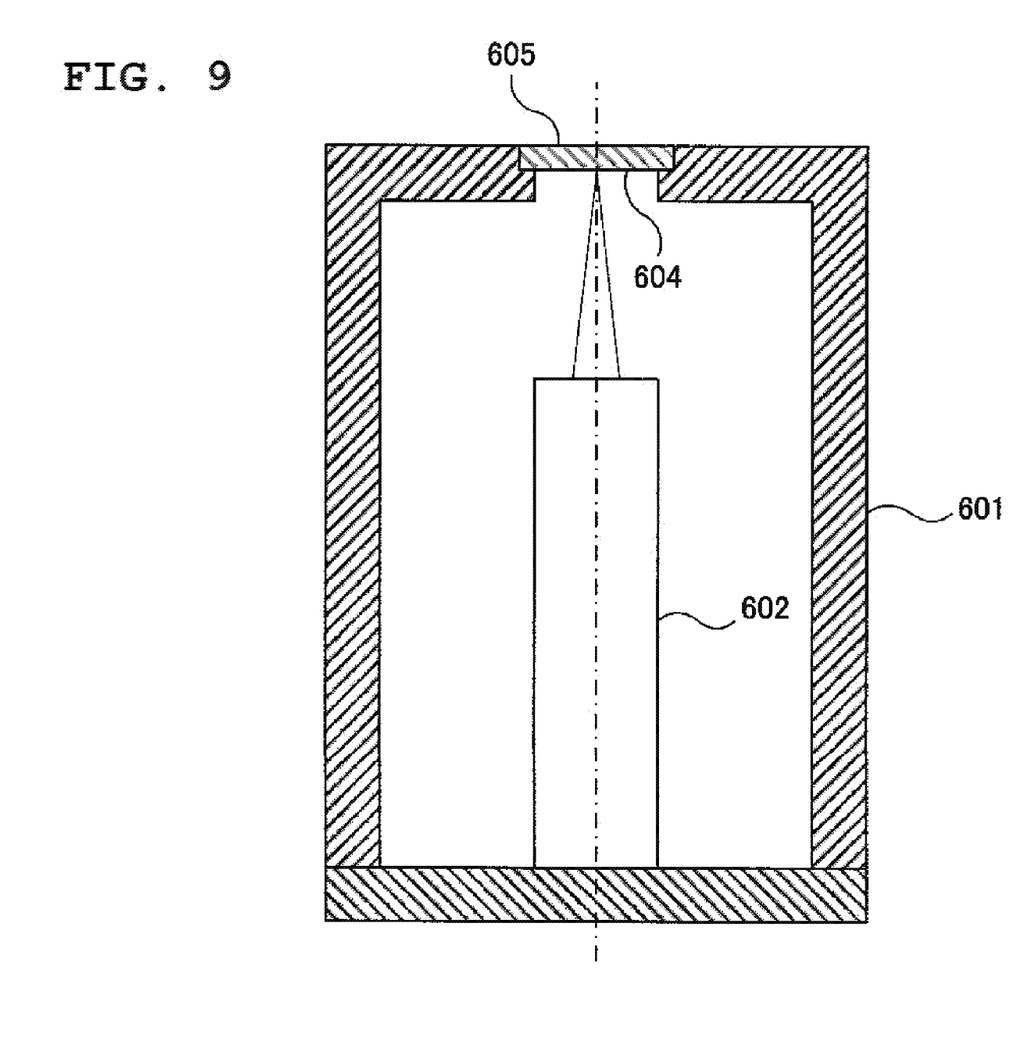
FIG. 9 is a schematic cross-sectional view similar to FIG. 8, using a sealed vacuum container.

However, if a rubber O-ring is used as described above, the degree of vacuum decreases gradually due to the gas transmission of the O-ring, and the evaporation of vacuum grease and the like. Hence, as in FIG. 8, it is effective against an open apparatus that always exhausts air by a vacuum pump such as a turbo-molecular pump. However, it is not possible to be applied to an x-ray generating apparatus using a seal-off vacuum container such as illustrated in FIG. 9, that is, a sealed x-ray generating apparatus. In other words, in the sealed apparatus illustrated in FIG. 9, an x-ray irradiation window 605 where a target 604 is integrally laminated and formed cannot maintain the degree of vacuum unless airtightly fixed by welding or brazing to a vacuum container 601 where an electron gun 602 is accommodated.

A structure where part of the vacuum container, together with the target and the x-ray irradiation window, is moved via the vacuum bellows can be applied to such a sealed apparatus. A configuration example of the case where the vacuum bellows is used is described based on FIG. 10 that is a schematic cross-sectional view of enlarged main parts in the vicinity of a target. In this example, a through hole 701a is formed in the top of a main body 701 of the vacuum container that accommodates an electron gun (not illustrated) and is fixed to an apparatus frame or the like. One end (lower end) of a vacuum bellows 702 is airtightly fixed to the periphery of the through hole 701a by welding or brazing. In addition, the other end (upper end) of the vacuum bellows 702 is airtightly fixed likewise to the periphery of a recess 703a that is formed in a moving member 703 and opens downward.

Figure 10:
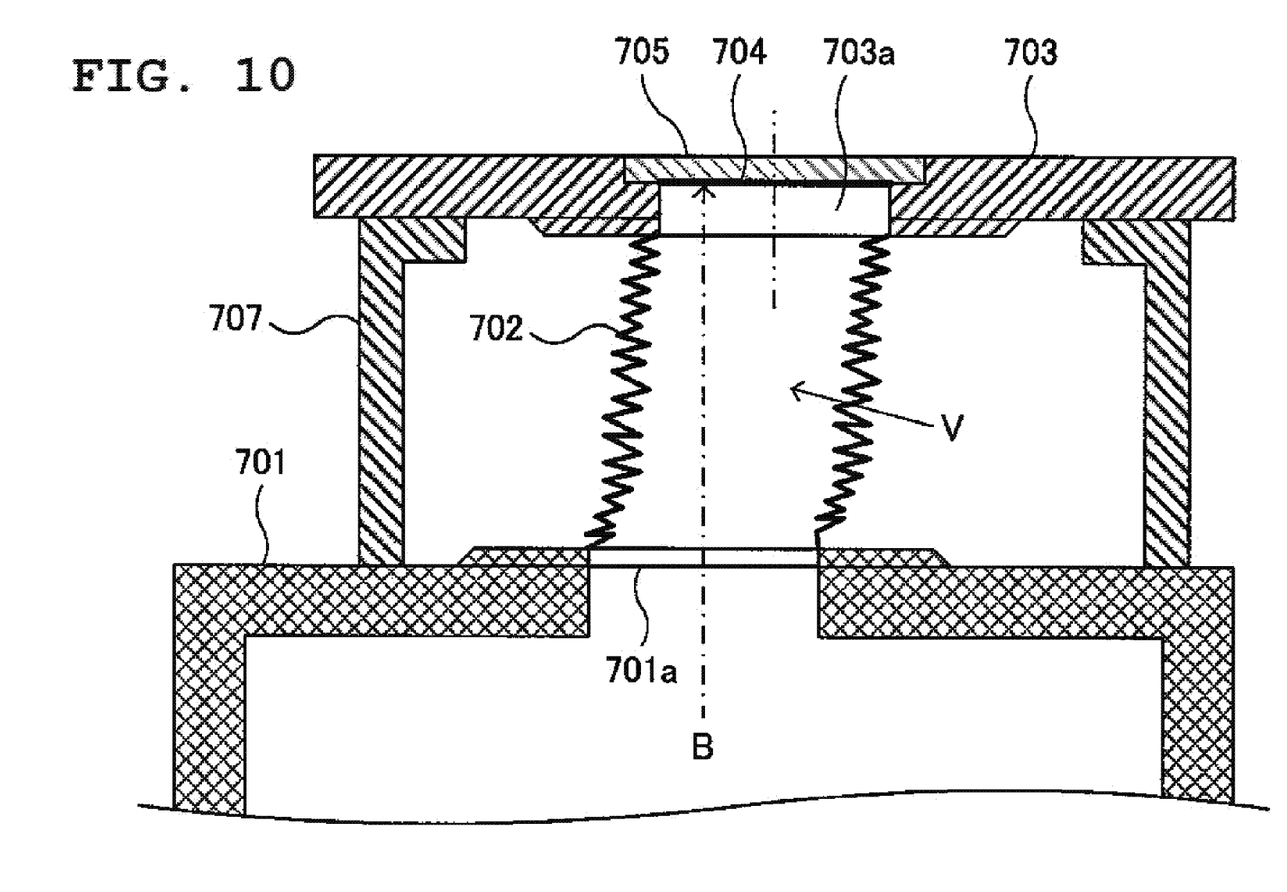
FIG. 10 is a schematic cross-sectional view illustrating a main part configuration example of the vicinity of a target of a case in which a position to irradiate a target with an electron beam is changed using a vacuum bellows.

An x-ray irradiation window 705 where a target 704 is laminated and formed is fixed to the moving member 703 in such a manner as to form a ceiling portion of the recess 703a. Therefore, a wall body of the main body 701 of the vacuum container, and the vacuum bellows 702 of which lower end communicates with the main body 701 and of which upper end is blocked by the x-ray irradiation window 705 serve as a wall body partitioning the inside and the outside of the vacuum container. An inner region V of them enters a vacuum state.

The electron beam B from the electron gun is applied from the main body 701 to the target 704 through the through hole 701a and the inside of the vacuum bellows 702. Consequently, the vacuum bellows 702 is bent to move the moving member 703. Accordingly, the position of irradiation of the electron beam B of the target 704 can be changed.

When, for example, an x-ray generating apparatus of this type is used for an x-ray test apparatus or the like, if space coordinates of an x-ray focal spot are changed, even if a sample is placed at the same location, a fluoroscopic region is changed. In addition, various readjustments such as reconfiguration of various parameters of an apparatus system and an adjustment to the position of an apparatus component are required, which is not preferable.

Therefore, in the configuration of FIG. 10, it is required to restrict the movement of the moving member 703 only to a direction orthogonal to the direction of irradiation of the electron beam B, that is, to prevent the target 704 from moving and inclining in an approaching/separation direction with respect to the electron gun. Therefore, in FIG. 10, a contact member 707 for guiding and the like are provided to the main body 701 to cause the moving member 703 to be displaced while coming into sliding contact with the contact member 707.

In the configuration of FIG. 10, a strong force acts on the vacuum bellows 702 in a direction of its contraction due to the pressure difference between the inside and the outside, that is, a direction toward the main body 701. Therefore, a strong frictional force works on a sliding surface between the contact member 707 on the main body 701 side and the moving member 703. Accordingly, it becomes impossible to move the moving member 703 easily. It becomes a practical problem. In order to solve the problem, it is also conceivable to apply a lubricant to the sliding surface. However, it is difficult to cause the movement with the same force for a long period of time.

Moreover, as described above, the x-ray generating apparatus using a transmission target is advantageous on the respect of being able to increase the fluoroscopic magnification, as compared to one using a reflection target. However, in order to achieve this, it is required to place an object at a position close to the x-ray irradiation window. Hence, providing a large structure near the x-ray irradiation window should be avoided as much as possible. In addition, it is not possible either to provide a space for reducing a sliding frictional force in a guide mechanism for regulating the displacement of the moving member with respect to the main body of the vacuum container.

The present invention has been made considering such circumstances. An objective of the present invention is to provide an x-ray generating apparatus that can easily displace a moving member that holds a target and an x-ray irradiation window with respect to a main body of a vacuum container with a light force with a compact mechanism, and can extend the life of the target without impairing an advantage being a high fluoroscopic magnification that can be obtained by using a transmission target.

SUMMARY OF THE INVENTION

An x-ray generating apparatus comprises: a vacuum container having a main body to which an electron gun is fixed, and a moving member coupled movably and airtightly to the main body via a vacuum bellows, the moving member being provided with a target and an x-ray irradiation window; and a guide mechanism, provided on an outer side of the vacuum container, for regulating the movement and inclination of the moving member in an approaching/separation direction with respect to the electron gun to maintain a distance between an electron beam irradiation surface of the target and the electron gun constant upon movement of the moving member. The guide mechanism includes a guide portion where a guide flat surface along a plane orthogonal to a central axis of the electron beam is formed, the guide portion being provided on the main body side, a guided portion where a guided flat surface facing the guide flat surface is formed, the guided portion being provided on the moving member side, and at least three rolling elements placed between the guide flat surface and the guided flat surface.

The rolling elements are balls, and the guide flat surface or the guided flat surface is provided with a regulation mechanism for regulating rolling areas of the individual balls to prevent the balls from deviating from regions respectively set for the balls around the central axis of the electron beam.

The regulation mechanism is a ring-shaped member fixed to the guide flat surface or the guided flat surface in such a manner as to surround the ball.

The regulation mechanism is a recess formed in the guide flat surface or the guided flat surface in such a manner as to accommodate the ball.

The regulation mechanism is a groove formed into a ring shape around the central axis of the electron beam in the guide flat surface or the guided flat surface, and a partition plate provided in the groove for regulating the circumferential movement of the ball in the groove.

An x-ray generating apparatus comprises: a vacuum container having a main body to which an electron gun is fixed, and a moving member coupled movably and airtightly to the main body via a vacuum bellows, the moving member being provided with a target and an x-ray irradiation window; and a guide mechanism, provided on an outer side of the vacuum container, for regulating the movement and inclination of the moving member in an approaching/separation direction with respect to the electron gun to maintain a distance between an electron beam irradiation surface of the target and the electron gun constant upon movement of the moving member. The guide mechanism includes a guide portion provided on the main body side, a guided portion provided on the moving member side, a flat surface formed on one of the guide portion and the guided portion, and at least three convex curved surfaces formed to be in contact with the flat surface on the other of the guide portion and the guided portion.

The convex curved surface is a spherical surface.

DETAILED DESCRIPTION OF THE EXEMPLARY EMBODIMENTS

The present invention is intended to solve the problem by holding a target movably with respect to an electron gun using a vacuum bellows, and reducing a frictional force acting on a guide mechanism for regulating the movement and attitude of the target to maintain the position of an x-ray focal spot constant with rolling contact using a rolling element or contact between a convex curved surface and a flat surface.

In other words, a moving member provided with the target and an x-ray irradiation window via the vacuum bellows is movably connected to a main body of a vacuum container. Accordingly, the degree of vacuum in the vacuum container is prevented from decreasing. In addition, the guide mechanism for regulating the movement direction and inclination of the target is provided on an outer side of the vacuum container to prevent the x-ray focal spot from moving upon movement of the target. The frictional force acting on a contact portion of the guide mechanism due to the contraction of the vacuum bellows caused by the pressure difference between the inside and the outside of the vacuum container can be significantly reduced by bringing the contact portion into rolling contact via the rolling element.

Moreover, the contact portion of the guide mechanism makes contact between the convex curved surface and the flat surface. Accordingly, it is possible to prevent the occurrence of, for example, a ringing phenomenon as in upon contact between flat surfaces and to reduce the frictional force although not as much as the rolling contact.

As long as the mutual positions of the rolling elements between a guide flat surface and a guided flat surface are not imbalanced largely, if there are three rolling elements at a minimum, they can support and move the moving member without inclining it. Moreover, balls are used as the rolling elements. Accordingly, the moving member can be moved along a guide surface in any direction.

Three or more balls are provided between the guide flat surface and the guided flat surface. In addition, a regulation mechanism that regulates the rolling areas of the balls is provided to prevent the positions of the individual balls from deviating from their regions set around the central axis of an electron beam. Accordingly, even if the mutual positions of the balls change gradually while the moving member is repeatedly moved, imbalances in the mutual positions of the balls can be restricted within the fixed areas. Moreover, the regulation mechanism is also useful in facilitating the handling of the ball upon assembly of the apparatus.

The regulation mechanism that regulates the rolling areas of the individual balls may be provided on either of the guide flat surface side or the guided flat surface side. Moreover, as a specific configuration of the regulation mechanism, for example, structures can be adopted in which rings that surround the periphery of each ball in its predetermined rollable region are fixed to either of the flat surfaces, in which pit-like recesses where the individual balls can secure their predetermined rollable regions are formed in either of the flat surfaces to accommodate the balls in their recesses, and in which a ring-shaped groove is formed in either of the flat surfaces and partition plates that partition the inside of the groove in the circumferential direction are provided to regulate the rolling areas of the individual balls.

If the contact portion of the guide mechanism makes contact between the convex curved surface and the flat surface, the ball is fixed, for example, to a guide portion or guided portion by welding, brazing, or the like to form a spherical surface. Accordingly, the production of the convex curved surface becomes easy.

According to the present invention, it is possible to easily move a target with respect to the position of irradiation of an electron beam with a light force while maintaining a high degree of vacuum. In addition, there is no need to provide a large structure to obtain this operation and effect. Accordingly, a fluoroscopic magnification is not influenced, either. From these points, the present invention can increase its effect especially when being applied to an x-ray generating apparatus including a transmission target using a sealed vacuum container.

Hereinafter, preferred embodiments of the present invention will be described with reference to the drawings.

Figure 1:
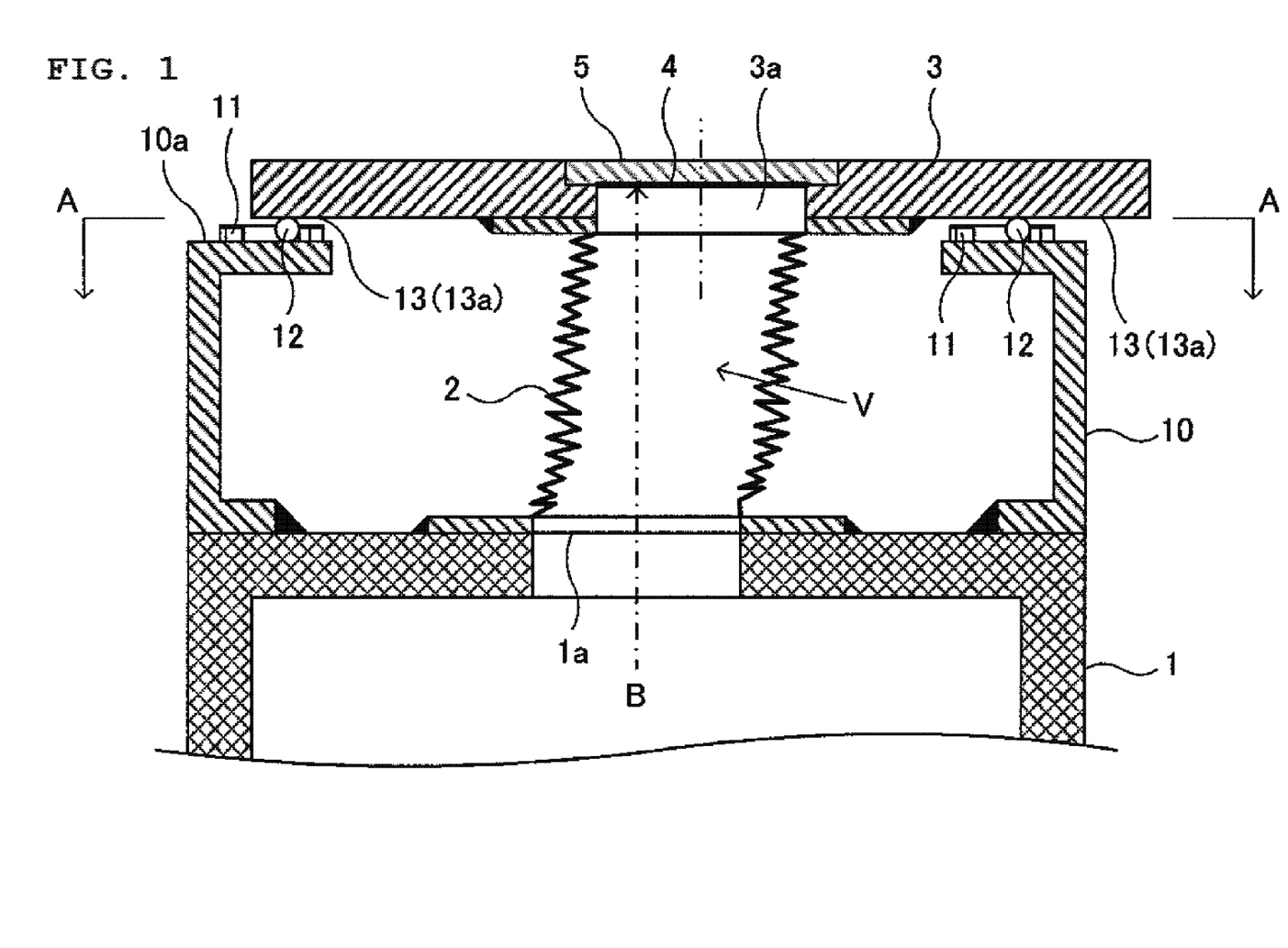
FIG. 1 is a schematic vertical cross-sectional view illustrating the vicinity of a target in an embodiment of the present invention.
Figure 2:
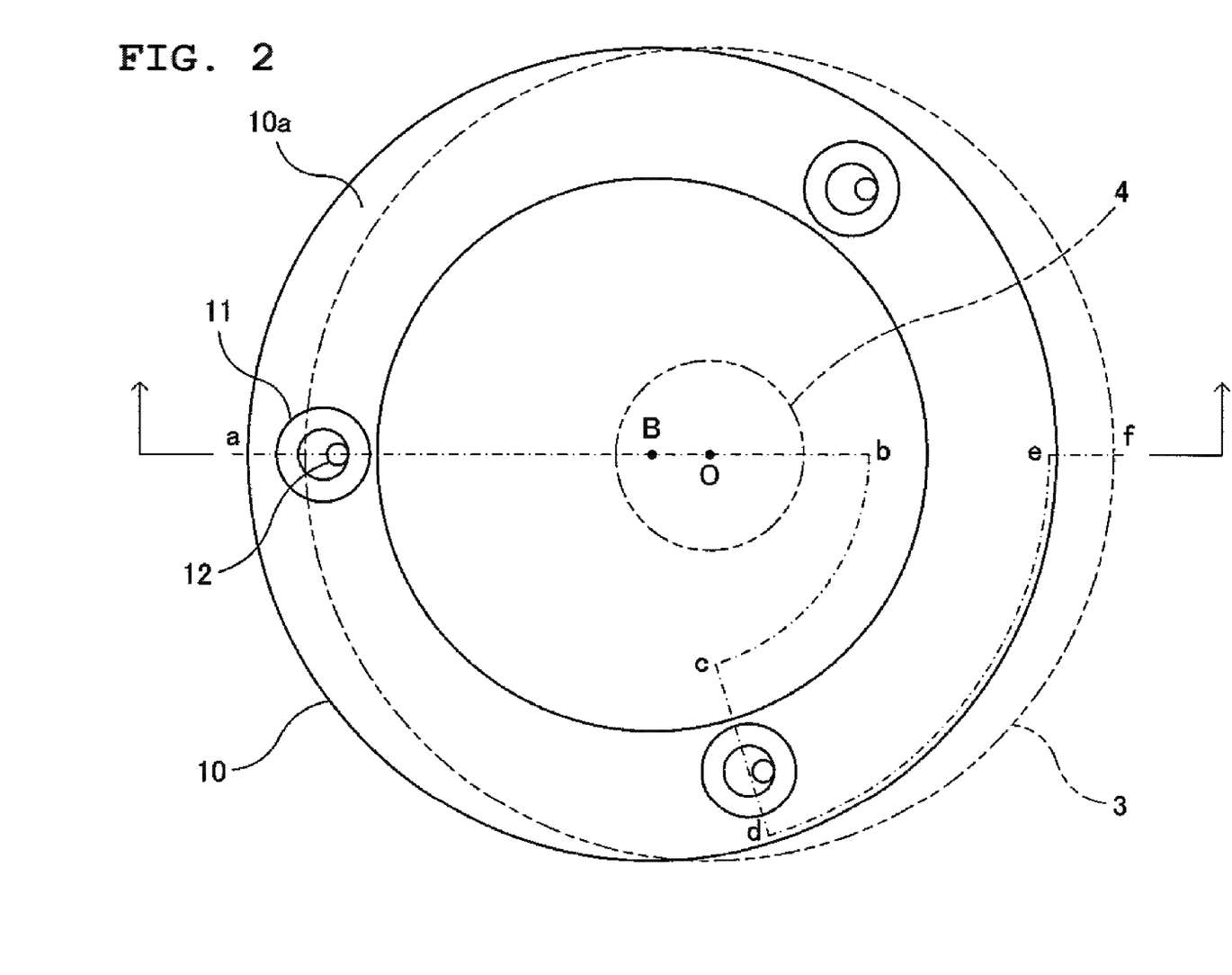
FIG. 2 is a cross-sectional view taken along line A-A in FIG. 1.

FIG. 1 is a vertical cross-sectional view schematically illustrating the vicinity of a target in an embodiment of the present invention. FIG. 2 is a cross-sectional view taken along line A-A in FIG. 1. FIG. 1 corresponds to a cross section taken along a-b-c-d-e-f in FIG. 2. Moreover, a basic configuration of an x-ray generating apparatus of the embodiment is assumed to use a sealed vacuum container and a transmission target as in the above FIG. 9.

The vacuum container illustrated in FIG. 1 includes a main body 1 in which an electron gun (not illustrated) is accommodated and fixed, and a moving member 3 airtightly coupled to the main body 1 via a vacuum bellows 2. In other words, a through hole 1a is formed in the top of the main body 1. One end of the vacuum bellows 2 is airtightly fixed to the periphery of the through hole 1a by welding or brazing. Similarly, the other end of the vacuum bellows 2 is airtightly fixed to the periphery of a recess 3a formed in the moving member 3.

An x-ray irradiation window 5 where a target 4 is laminated and formed is fixed to the moving member 3 in such a manner as to form a ceiling portion of the recess 3a. Consequently, a wall body of the main body 1 and the vacuum bellows 2 lower end of which communicates airtightly with the main body 1 and upper end of which is blocked by the x-ray irradiation window 5 serve as a wall body forming the vacuum container. An inner region V of them is in an evacuated state.

An electron beam B from the electron gun fixed to the main body 1 side is applied from the main body 1 to the target 4 through the through hole 1a and the inside of the vacuum bellows 2.

A ring-shaped guide portion 10 is fixed to an upper surface of the main body 1 in such a manner as to surround the outside of the vacuum bellows 2. A guide flat surface 10a along a plane orthogonal to the central axis of the electron beam B is formed on an upper surface of the guide portion 10.

On the other hand, a guided flat surface 13a is formed on a lower surface of the moving member 3 in such a manner as to face the guide flat surface 10a. This portion forms a guided portion 13. Three balls (steel balls) 12 of the same size are interposed between the guide flat surface 10a and the guided flat surface 13a.

The balls 12 are placed, one by one, in three rings 11 fixed to the guide flat surface 10a as illustrated in FIG. 2. Consequently, the mutual positional relationship of the balls 12 is regulated to positions obtained by roughly trisecting the periphery of the central axis of the electron beam B. The mutual positional relationship is not largely imbalanced. In other words, the rings 11 are fixed at positions obtained by trisecting a circle with the central axis of the electron beam B as the center of the circle. The rolling area of each ball 12 placed in each ring 11 is restricted to the inside of the ring 11. Consequently, as described below, when the moving member 3 is repeatedly moved, even if the mutual positional relationship of the balls 12 is displaced to some extent by the rolling of the balls 12 upon the movement, the positional relationship of the balls 12 is not largely imbalanced due to the regulation by the rings 11.

Moreover, the presence of the ring 11 regulates the position of the ball 12 on the guide flat surface 10a upon assembly of the apparatus. Accordingly, there is also an advantage in facilitating the handling of the ball 12.

In the above configuration, the vacuum bellows 2 contracts due to the pressure difference between the inside and the outside of the vacuum container. The guided flat surface 13a provided to the moving member 3 enters a state of being pressed against the balls 12. Consequently, the moving member 3 enters a state of being supported by the guided flat surface 10a via the three balls 12 of the same size on the guided flat surface 13a, and becomes oriented along a direction orthogonal to the central axis of the electron beam B.

It is simply required to apply a force from any horizontal direction to move the moving member 3. At this point in time, a downward strong force is acting on the moving member 3 due to the contraction of the vacuum bellows 2 caused by the pressure difference between the inside and the outside of the vacuum container. However, the balls 12 that come into rolling contact with the guided flat surface 13a formed on the lower surface of the moving member 3 and the guide flat surface 10a on the main body 1 side are interposed between the flat surfaces. Accordingly, the frictional resistance is significantly reduced as compared to a case where the flat surfaces are in surface contact with each other. Accordingly, the movement is easily performed with a light force.

A point that requires a special focus in the above embodiment is a point where the frictional resistance of the guide mechanism that regulates the movement of the moving member 3 is reduced with a very compact configuration. There is no structure, projection, and the like outward of the x-ray irradiation window 5 in the x-ray irradiation direction. Accordingly, the present invention can be applied without damaging at all the high fluoroscopic magnification, which is the advantage of the x-ray generating apparatus using the transmission target.

In the above example, the example using three balls as rolling elements is presented. However, as long as the number of rolling elements is three or more, it is not especially limited.

Figure 3A:
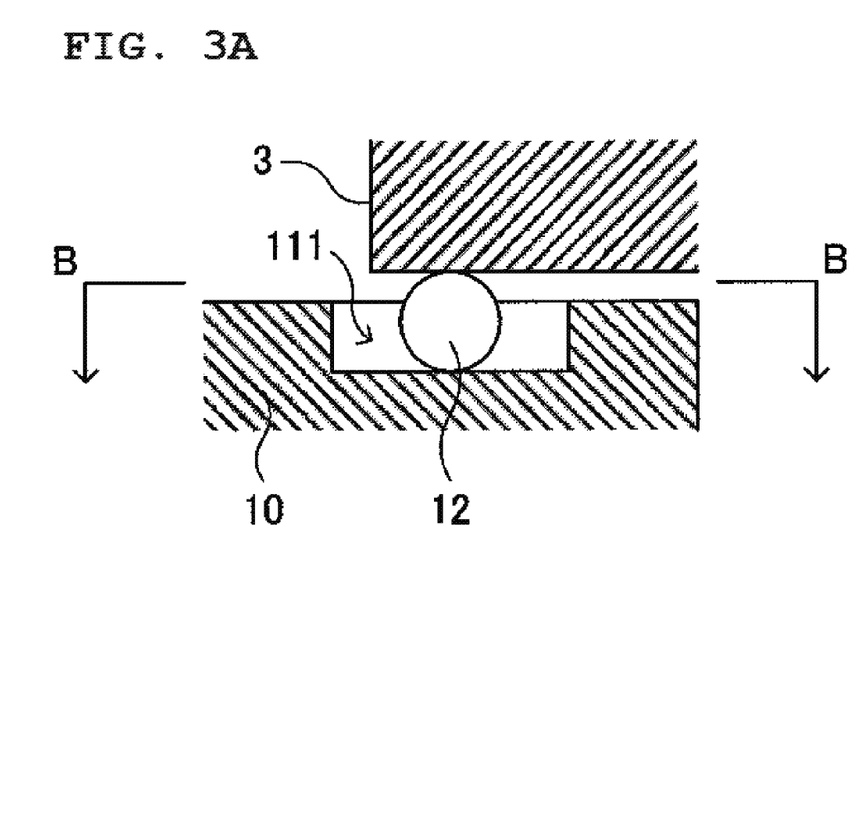
FIGS. 3A and 3B are cross-sectional views of main parts illustrating the vicinity of a ball in another embodiment of the present invention.
Figure 3B:
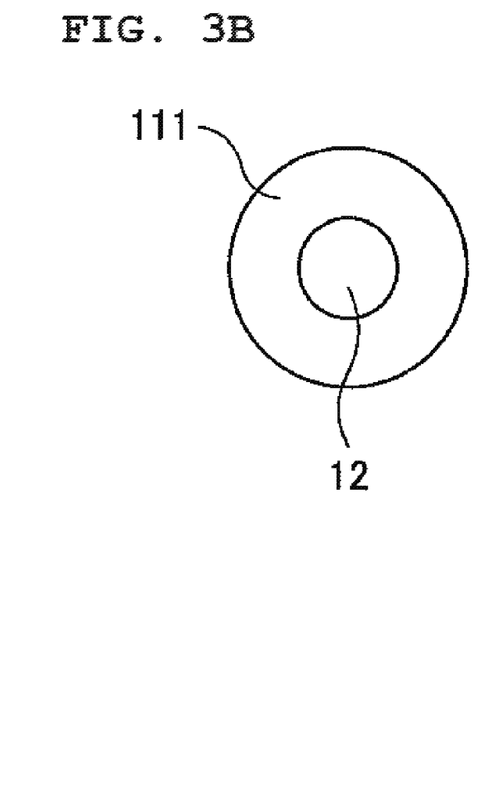

As the mechanism that regulates the rolling area of the ball 12, configurations illustrated in FIGS. 3A, 3B, 4A and 4B can be adopted in addition to the use of such a ring 11 as described above. FIGS. 3A and 3B illustrate another configuration example of the vicinity of the rolling element (ball). FIG. 3A is a vertical cross-sectional view illustrating main parts. FIG. 3B is a cross-sectional view taken along line B-B of FIG. 3A. In the configuration illustrated in FIGS. 3A and 3B, a plurality of recesses 111 is formed in the upper surface of the guide member 10. The balls 12 are placed, one by one, in the recesses 111. The rolling area of the ball 12 is restricted to the inside of the recess 111.

Figure 4A:
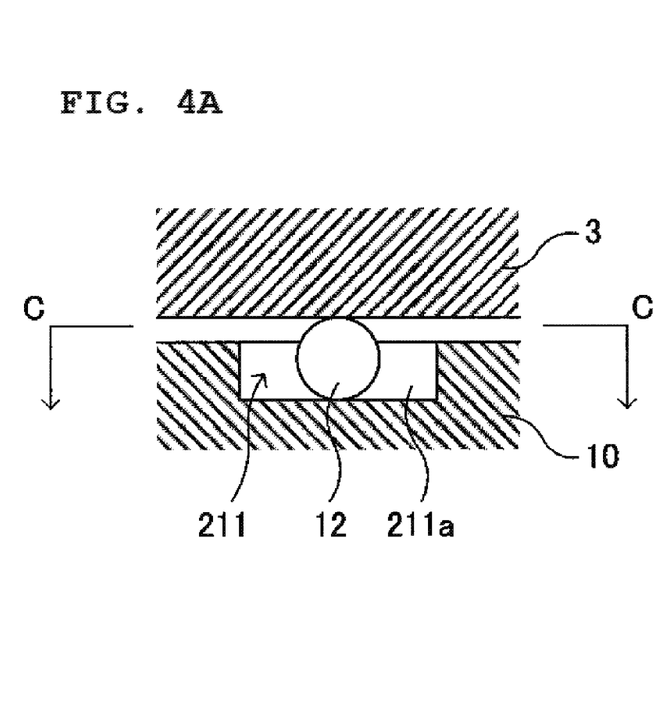
FIGS. 4A and 4B are cross-sectional views of main parts illustrating the vicinity of a ball in still another embodiment of the present invention.
Figure 4B:
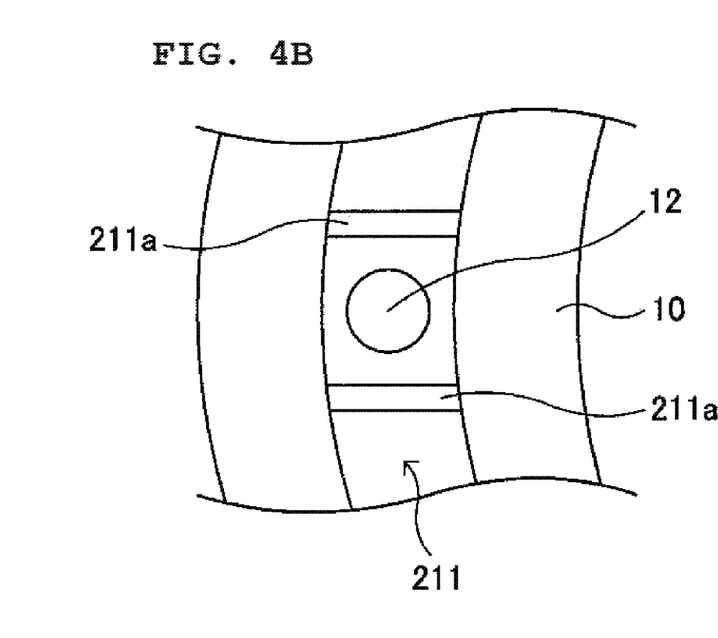

Moreover, FIGS. 4A and 4B illustrate still another configuration example of the vicinity of the rolling element (ball). FIG. 4A is a vertical cross-sectional view illustrating main parts. FIG. 4B is a cross-sectional view taken along line C-C of FIG. 4A. In the configuration illustrated in FIGS. 4A and 4B, a ring-shaped groove 211 is formed in the upper surface of the guide member 10 with the central axis of the electron beam B as the center of a circle. A plurality of the balls 12 is placed in the groove 211. In addition, the rolling areas of the individual balls 12 in the circumferential direction in the groove 211 are restricted by pairs of partition plates 211a fixed in the groove 211.

The rolling area regulation mechanism including the rings 11, the recesses 111, or the grooves 211 and the partition plates 211a such as described above is provided on the guide portion 10 side of the main body 1 as illustrated in the above examples. Alternatively, also if the regulation mechanism is provided on the guided portion 13 side of the moving member 3, an equivalent operation and effect can be exerted.

In the above embodiment, a mechanism that moves the moving member 3 is not limited at all. However, an example of the mechanism is conceptually illustrated in FIGS. 5A and 5B. FIG. 5B presents a state where an eccentric ring 14 is rotated 180° from the state of FIG. 5A.

Figure 5A:
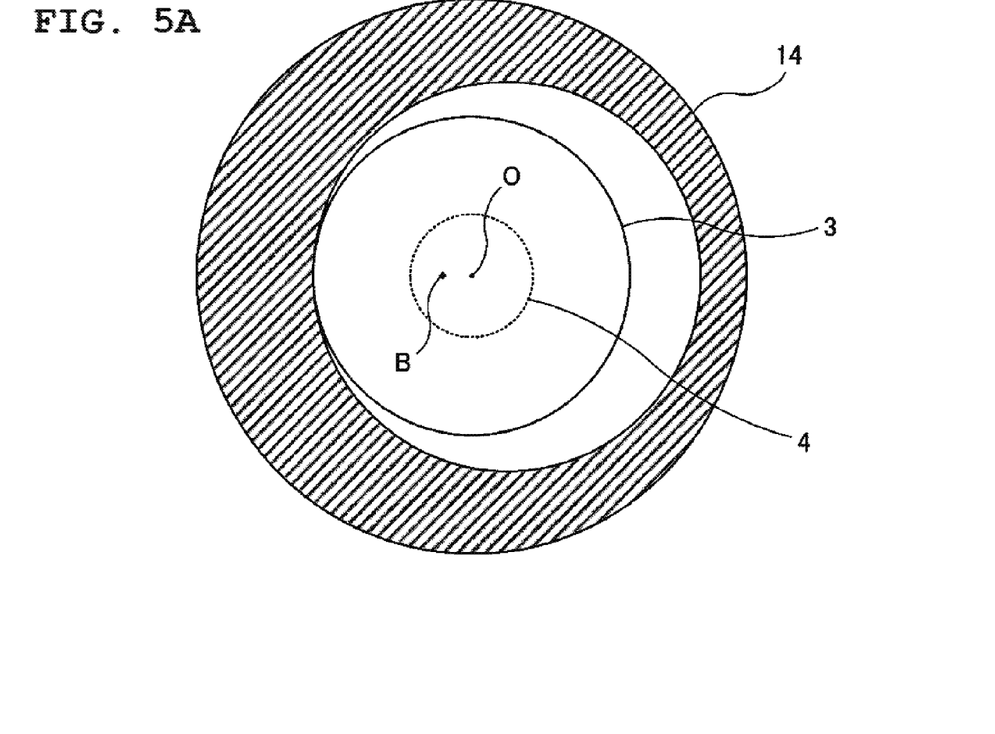
FIGS. 5A and 5B are conceptual diagrams illustrating an example of a moving mechanism that is applicable to the embodiment of FIG. 1.
Figure 5B:
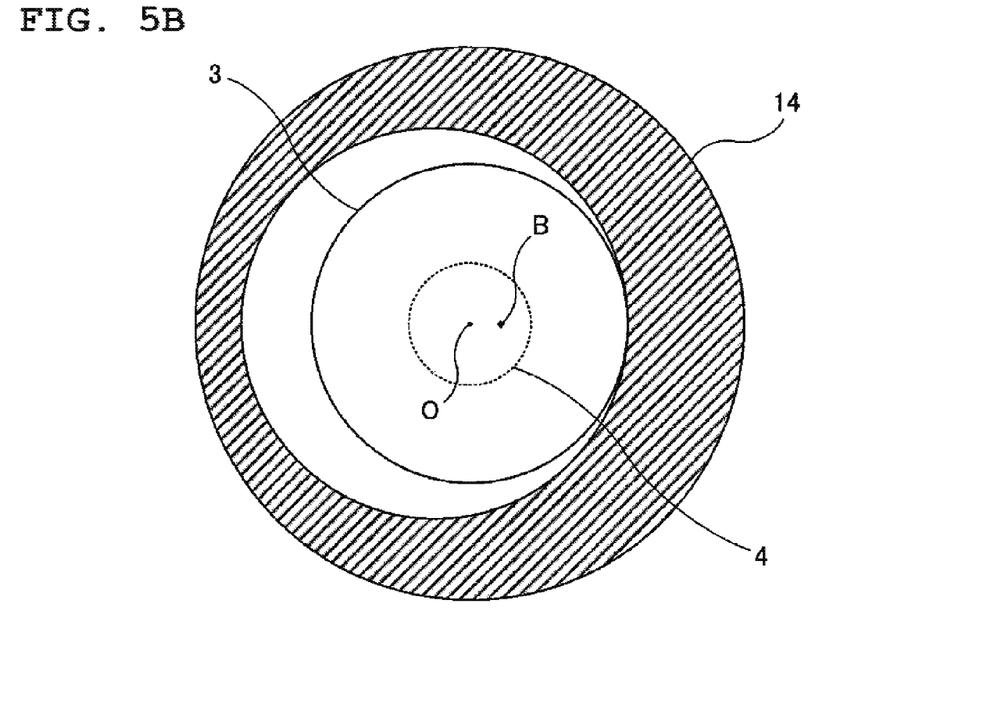

As illustrated in FIGS. 5A and 5B, it is possible to be configured as follows: the eccentric ring 14 having an inner peripheral surface that is eccentric with respect to an outer peripheral surface is placed outward of the moving member 3; the eccentric ring 14 is rotated about the central axis of the electron beam B relative to the outer peripheral surface; accordingly, the inner peripheral surface comes into contact with an outer peripheral surface of the moving member 3; hence, a center O of the moving member 3 is decentered from the central axis of the electron beam B.

As is clear from FIGS. 5A and 5B, the moving member 3 can be decentered from the central axis of the electron beam B in a direction in accordance with the rotation position of the eccentric ring 14, which in turn can change the irradiation position of the electron beam B of the target 4 over 360° on a circle a predetermined distance away from the center O of the moving member 3.

Figure 6:
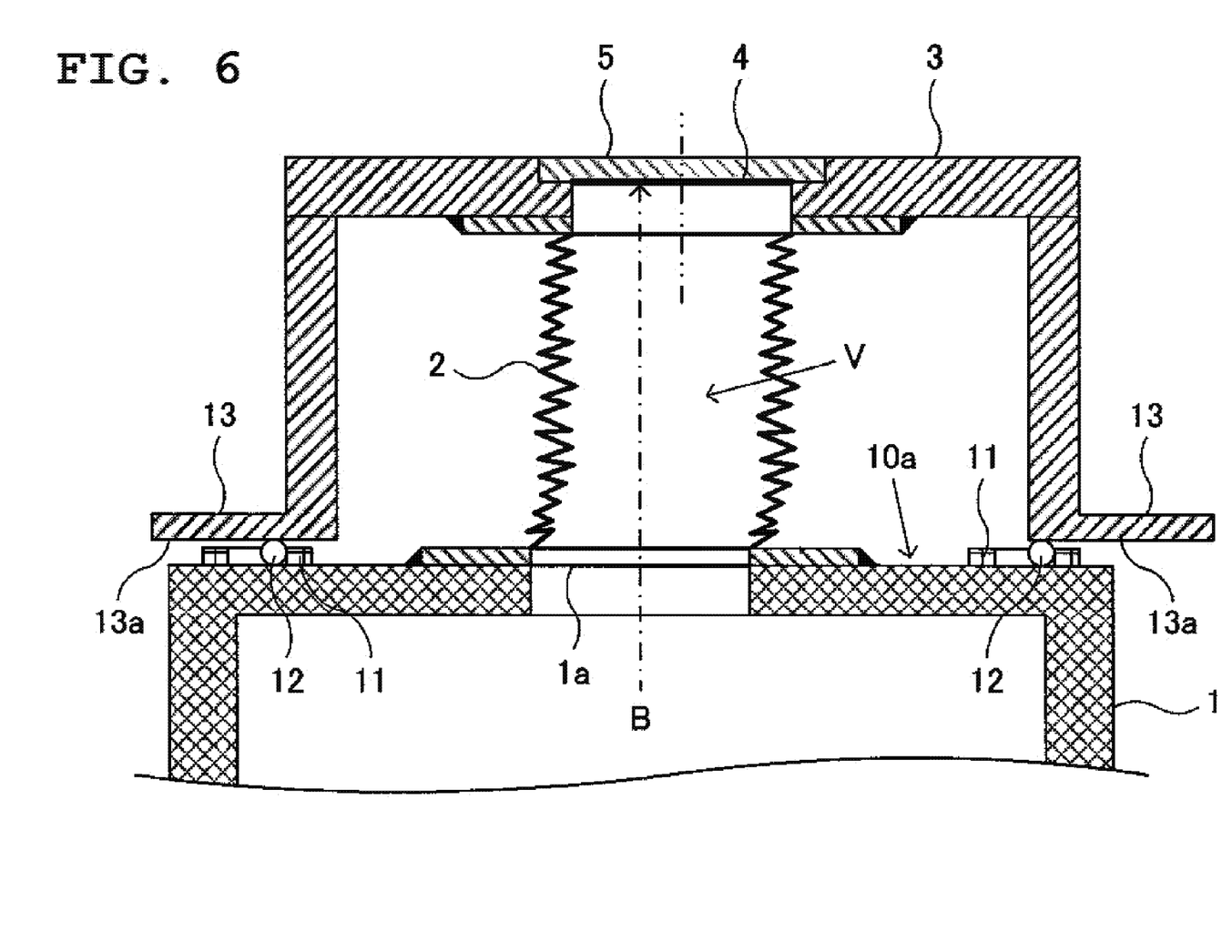
FIG. 6 is a schematic vertical cross-sectional view illustrating the vicinity of a target in yet another embodiment of the present invention.

In the above embodiment, the example is illustrated in which the guide portion 10 is fixed to the upper surface of the main body 1 of the vacuum container and is erected, and the guide flat surface 10a is formed on the upper surface of the guide portion 10. However, for example, as illustrated in FIG. 6, it may be configured as follows: while the upper surface of the main body 1 serves as the guide flat surface 10a as in the above embodiment, the guided portion 13 is fixed to the lower surface of the moving member 3, facing downward; the guided flat surface 13a is formed on a lower surface of the guided portion 13; a plurality of the balls 12 is interposed between these flat surfaces. Also in this case, the rolling area regulation mechanism such as the rings 11 provided on either of the guide flat surface 10a or the guided flat surface 13a regulates the rolling areas of the balls 12. Also in this case, it is possible to exert the totally equivalent operation and effect to the above examples.

Moreover, in the above embodiment, the example in which a ball is used as the rolling element is illustrated. However, the present invention does not necessarily require the use of a ball and can use another rolling element, for example, a cylindrical roller. However, the cylindrical roller can roll only in one direction. Accordingly, the movement of the moving member is restricted to a one-dimensional direction. Therefore, if the cylindrical roller is used, it is possible to adopt a configuration in which, for example, guide grooves parallel to each other along the rolling direction of the cylindrical roller are provided at both sides of and across the central axis of an electron beam in the guide flat surface or guided flat surface, and a plurality of cylindrical rollers is accommodated in the guide grooves to guide an end surface of each cylindrical roller, and also, partition plates or the like are provided in the rolling direction to prevent the individual cylindrical rollers from becoming imbalanced.

Furthermore, also if grooves of which cross sections are v-shaped (V grooves) are formed parallel at both sides of and across the central axis of an electron beam in the guide flat surface, and balls are placed in the V grooves, they can roll only in one direction. A similar operation and effect to the above cylindrical roller are exerted. It cannot be said that the V groove is literally a flat surface. However, linear positions (four straight lines) with which the balls placed in the two V grooves come into contact are included in one flat surface. Accordingly, in the present description, such a configuration is also assumed to be included in the guide flat surface of the present invention.

The above examples illustrate examples in which the objective of the present invention is achieved using rolling elements. However, the present invention is not limited to them. An objective effect in accordance with the above examples can also be exerted by a configuration in which the flat surface and the convex curved surface are brought into contact with each other. In the configuration in this case, instead of the balls 12 in the embodiment illustrated in FIGS.

1 and 2, for example, a plurality of convex curved surfaces is formed protruding from the upper surface of the guide portion 10. The convex curved surfaces are brought into contact with the guided flat surface 13a on the moving member 3 side. In this case, naturally, the rings 11 are not required.

Figure 7:
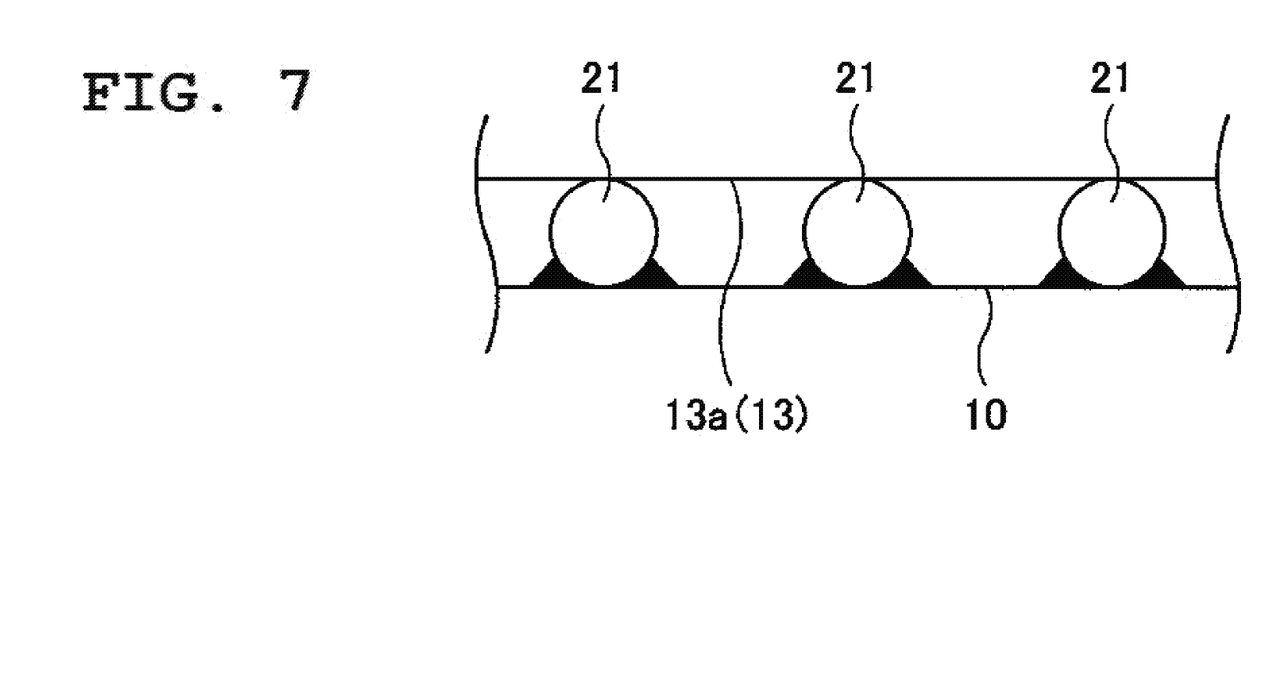
FIG. 7 is a schematic diagram illustrating the structure of a contact portion of a case where a guide mechanism makes sliding contact between a convex curved surface and a flat surface.

However, it is not easy to form a plurality of convex curved surfaces protruding from a member. Accordingly, it is simply required to adopt, for example, a method in which balls (steel balls) 21 are fixed to a surface of the guide portion 10 by welding, brazing, or the like, as illustrated in FIG. 7. It is simply required to bring the tops of the balls 21 into contact with the guided flat surface 13a.

According to the above configuration, the guide portion 10 comes into sliding contact with the guided portion 13 (the guided flat surface 13a). Therefore, the effect of reducing the frictional resistance is slightly reduced as compared to the previous examples in which they come into rolling contact using the rolling elements 12. However, the frictional resistance can be reduced as compared to the case in which the flat surfaces are brought into sliding contact with each other. Moreover, the ringing phenomenon caused upon contact between the flat surfaces can be prevented.

In the case of adopting the above configuration in which a convex curved surface and a flat surface are combined, naturally, the convex curved surface may be provided on the guide portion 10 side of the main body 1, the guided flat surface 13a may be formed on the guided portion 13 side of the moving member 3, the convex curved surface may be provided on the guided portion 13 side of the moving member 3, and the guide flat surface 10a may be formed on the guide portion 10 side of the main body 1. Moreover, the number of convex curved surfaces formed can be set to any number as long as it is three or more.

What is claimed is:

1. An x-ray generating apparatus comprising:
   a vacuum container having a main body to which an electron gun is fixed, and a moving member coupled movably and airtightly to the main body via a vacuum bellows, the moving member being provided with a target and an x-ray irradiation window; and
   a guide mechanism, provided on an outer side of the vacuum container, for regulating the movement and inclination of the moving member in an approaching/separation direction with respect to the electron gun to maintain a distance between an electron beam irradiation surface of the target and the electron gun constant upon movement of the moving member, wherein
   the guide mechanism includes
      a guide portion where a guide flat surface along a plane orthogonal to a central axis of the electron beam is formed, the guide portion being provided on the main body side,
      a guided portion where a guided flat surface facing the guide flat surface is formed, the guided portion being provided on the moving member side, and
      at least three rolling elements placed between the guide flat surface and the guided flat surface.

2. The x-ray generating apparatus according to claim 1, wherein
   the rolling elements are balls, and
   the guide flat surface or the guided flat surface is provided with a regulation mechanism for regulating rolling areas of the individual balls to prevent the balls from deviating from regions respectively set for the balls around the central axis of the electron beam.

3. The x-ray generating apparatus according to claim 2, wherein the regulation mechanism is a ring-shaped member fixed to the guide flat surface or the guided flat surface in such a manner as to surround the ball.

4. The x-ray generating apparatus according to claim 2, wherein the regulation mechanism is a recess formed in the guide flat surface or the guided flat surface in such a manner as to accommodate the ball.

5. The x-ray generating apparatus according to claim 2, wherein the regulation mechanism is a groove formed into a ring shape around the central axis of the electron beam in the guide flat surface or the guided flat surface, and a partition plate provided in the groove for regulating the circumferential movement of the ball in the groove.

6. An x-ray generating apparatus comprising:
   a vacuum container having a main body to which an electron gun is fixed, and a moving member coupled movably and airtightly to the main body via a vacuum bellows, the moving member being provided with a target and an x-ray irradiation window; and
   a guide mechanism, provided on an outer side of the vacuum container, for regulating the movement and inclination of the moving member in an approaching/separation direction with respect to the electron gun to maintain a distance between an electron beam irradiation surface of the target and the electron gun constant upon movement of the moving member, wherein
   the guide mechanism includes
      a guide portion provided on the main body side,
      a guided portion provided on the moving member side,
      a flat surface formed on one of the guide portion and the guided portion, and
      at least three convex curved surfaces formed to be in contact with the flat surface on the other of the guide portion and the guided portion.

7. The x-ray generating apparatus according to claim 6, wherein the convex curved surface is a spherical surface.

* * * * *